United States Patent [19]

Blackmon

[11] Patent Number: 4,484,917
[45] Date of Patent: Nov. 27, 1984

[54] FEMALE EXTERNAL CATHETER

[75] Inventor: Gene D. Blackmon, Dallas, Tex.

[73] Assignee: The Dallas Venture, Dallas, Tex.; a part interest

[21] Appl. No.: 531,160

[22] Filed: Sep. 9, 1983

Related U.S. Application Data

[63] Continuation of Ser. No. 294,979, Aug. 21, 1981, abandoned.

[51] Int. Cl.$^3$ ............................................. A61M 1/00
[52] U.S. Cl. ................................... 604/327; 604/328; 604/329; 4/144.3
[58] Field of Search ............... 128/294, 295, 761, 769; 4/144.1–144.4; 604/327–331

[56] References Cited

U.S. PATENT DOCUMENTS

| | | | |
|---|---|---|---|
| 1,951,871 | 3/1934 | Judah | 4/144.3 |
| 2,548,149 | 4/1951 | Fowler | 128/295 |
| 2,904,047 | 9/1959 | Hamilton | 128/295 |
| 3,200,415 | 8/1965 | Breece | 4/110 |
| 3,340,876 | 9/1967 | Hill | 128/295 |
| 3,374,790 | 3/1968 | Mayhorne | 128/295 |
| 3,401,697 | 9/1968 | Lefley | 128/295 |
| 3,406,690 | 10/1968 | Igel | 128/295 |
| 3,556,102 | 1/1971 | Davis | 128/295 |
| 3,613,122 | 10/1971 | Gross | 4/110 |
| 3,964,111 | 6/1976 | Packer | 128/295 |
| 4,187,851 | 2/1980 | Hauser | 128/295 |
| 4,198,979 | 4/1980 | Cooney | 128/295 |
| 4,233,978 | 11/1980 | Hickey | 128/295 |

FOREIGN PATENT DOCUMENTS

| | | | |
|---|---|---|---|
| 1004104 | 12/1972 | Canada | 128/295 |
| 23942 | 2/1981 | European Pat. Off. | 128/295 |

Primary Examiner—C. Fred Rosenbaum
Assistant Examiner—J. L. Kruter
Attorney, Agent, or Firm—Thomas L. Cantrell; Warren B. Kice; Stanley R. Moore

[57] ABSTRACT

An external catheterization device and technique is disclosed that provides for increased safety, comfort and mobility. The device is constructed from four major elements, an adhesive surface, a pliable stabilizer, a main body and an outlet tube. The adhesive surface covers the subject side of the stabilizer and surrounds the inlet to the main body of the catheter. The stabilizer is formed of a material conformable to the subject and aids in placing the catheter. The main body of the catheter is formed to carry urine and vaginal discharge which is received through the inlet, to the outlet tube at which conventional drainage devices are attachable. The catheterization technique necessary for utilizing the external catheter of the present requires cleansing the entire urogenital area applying a suitable protective dressing, and pressing the adhesive surface of the catheter into a leak resistent, sealing relationship with the subject's body. The adhesive surface surrounding the open inlet contacts the subject's body about the clitoris, about opposite sides of the urethra and vagina between the labum majora and labium minora and at the posterior fourchette. The main body of the catheter is proportioned to receive the opposing labium minora which should be extended therein through the inlet.

3 Claims, 3 Drawing Figures

FEMALE EXTERNAL CATHETER

This is a continuation of application, Ser. No. 294,979, now abandoned filed Aug. 21, 1981.

BACKGROUND OF THE INVENTION

The options of catheterization techniques currently available to girls and women are extremely limited. More particularly, external catheterization techniques that are available for females remain so unsatisfactory that the use of internal catheterization remains the more prevalent medical practice. However, indwelling catheters cause considerable discomfort and restrict the mobility of the subject. Even more important, the use of common internal catheterization techniques have been linked to an alarmingly high incidence of bladder infections. Normal body defense mechanism are also agitated by the presence of internal catheters and the body responds with rejection reactions. Finally, the body's reaction to indwelling catheters forces many women to go on regular schedules of intermittent catherization every few hours or so.

Thus, there is a long felt need for an external catherization device and technique that is safe, yet comfortable and secure. Further, the catheter should retain these attributes when worn for extended periods. It is also preferred that the catheterization technique be simple enough that an average subject may herself safely perform the catheterization and that the device be inexpensive enough to be disposable.

SUMMARY OF THE INVENTION

The present invention is a catheterization device and technique that satisfies these needs. The device itself is simply constructed with a minimum of members, each of which is formed through inexpensive manufacturing techniques operating upon inexpensive materials. The result is a catheter that may be used once, then disposed of. This disposability is particularly important for devices that are used by non-medical personnel, outside of hospitals or doctor's offices and the attendant sterilization equipment.

The catheter is formed from four major elements, an adhesive surface, a pliable but resilient stabilizer, a main body and an outlet tube.

The adhesive surface of the catheter covers the subject side of the stabilizer and surrounds the inlet to the main body of the catheter. The stabilizer is formed of a material sufficiently pliant to conform to accomodate the shape of the subject's body, but has sufficient rigidity to aid in placing the unit and to prevent the adhesive surface from folding over and sealing upon itself. The total area of adhesive surface presented to seal body contact around the inlet is increased by providing laterally appended shoulders to the stabilizer and extending the adhesive coating over these.

The main body of the catheter is formed to carry urine and vaginal discharge which is received through the inlet to the outlet tube at which conventional and well known drainage and collection devices are attachable.

A new catheterization technique is necessary for utilizing the external catheter of the present invention. Preparation for placing the catheter begins with trimming the pubic hair immediately adjacent the labium majora. This area is not affected directly, but the hair should be trimmed to prevent possible entanglement when the unit is placed.

Next, the entire urogenital area should be throughly cleansed and then the tender tissue to which the catheter unit is to be sealingly affixed mist be protected. Suitable protective dressings are well known in the art and such a dressing should be applied around the clitoris, in between the labium majora and the labium minora and down to the posterior fourchette. The protective dressing should then be allowed to throughly dry.

The adhesive surface of the catheter unit is then placed and pressed into a leak resistent sealing relationship with the subject's body. The adhesive surface surrounding the open inlet contacts subject's body about the clitoris, about opposite sides of the urethra and vagina and at the posterior fourchette. The adhesive surface upon the shoulders of the stabilizer further secures the catheter unit in position by providing extended adhesive surfaces for contact between the labium majora and labium minora.

The main body of the catheter is so proportioned to receive the opposing labium minora which should be extended therein through the inlet.

After checking to insure that a good seal has been secured that is not subject to possible leakage, a conventional drainage and collection system is attached to the end of the outlet tube.

A BRIEF DESCRIPTION OF THE DRAWINGS

DETAILED DESCRIPTION OF THE PREFERRED EMBODIMENT

Figure 2:
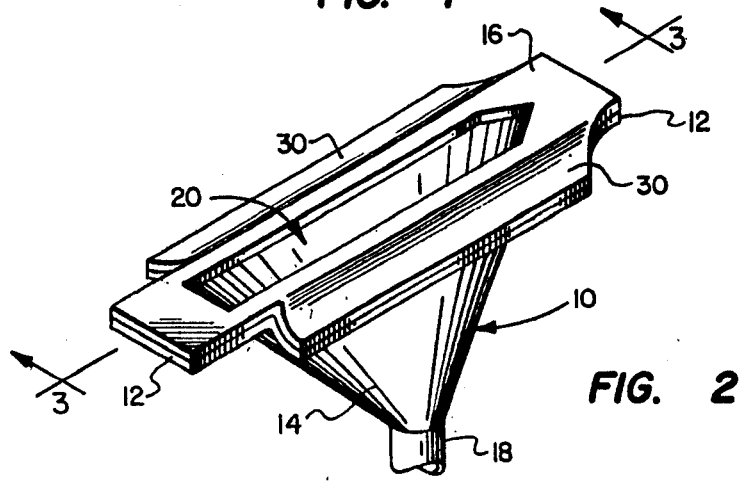
FIG. 2 is a perspective view of a catheter of the present invention.

FIG. 2 is a perspective view of the device illustrating a catheter of the present invention generally designated as catheter unit 10. The major elements of catheter 10 are stabilizer 12, main body 14, adhesive surface 16 and outlet tube 18.

Adhesive surface 16 surrounds inlet 20, and upon contact, seals the catheter against the subject's body in a leak-proof manner. The adhesive surface also secures the catheter in place. Adhesive surface 16 is supported by stabilizer 12 and is conveniently provided by proportioned double-sided adhesive tape.

Stabilizer 12 needs to be sufficiently pliable to readily conform to the shape of the subject's engaging surfaces, yet offer enough rigidity to both prevent adhesive surface 16 from folding upon itself and to maintain the opening of inlet 20 during placement. The preferred material that offers this combination of pliability and rigidity is slightly resilient, thin sheet plastic that has been cut into strips. Further, to increase the contact area provided by adhesive surface 16 yet operate within the necessary dimensional constraints, it is preferred that receding shoulders 30 be formed laterally along the stabilizer.

Figure 3:
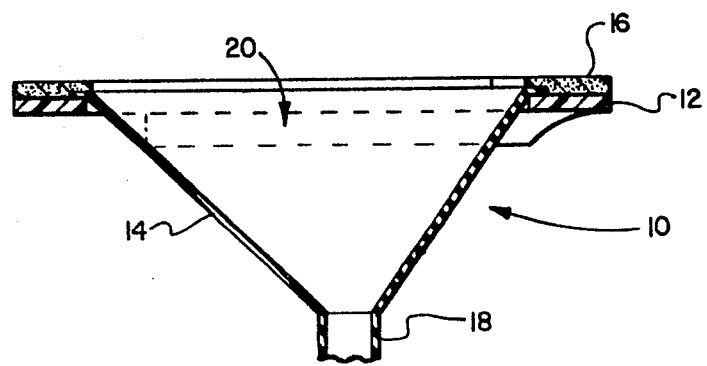
FIG. 3 is a longitudinal cross-sectional view of the catheter of the present invention taken along line 3—of FIG. 2.

FIG. 3 is a cross-section of the catheter illustrated in FIG. 2, taken along line 3—3 in that Figure. FIG. 3 best illustrates the connection of main body 14 to stabilizer 12 at inlet 20. Main body 14 must be securely sealed about the periphery of inlet 20 and it is convenient in the preferred embodiment to connect main body 14 to plastic stablizer 12 between a stabilizer and the double-sided adhesive tape which provides adhesive surface 16.

It is further preferred that main body 14 be formed of latex rubber and be so dimensioned that a standard sized catheter constructed in accordance with the present invention is sufficiently versatile to accomodate the structurally diverse labium minora presented by a range of young women, older women and mothers of any age. However, despite this versatility, there are individuals outside the anticipated normal standard size range which require special sizes such as sizes for young girls.

Main body 14 connects the flow path from inlet 20 to outlet tube 18 in order to carry urine and vaginal discharge to a discharge and collection system connected to the distal end of outlet tube 18. In the preferred embodiment, outer tube 18 is formed of latex rubber and is connected to a conventional legbag. Suitable collection systems are well known in the art and are deleted from the figures.

Figure 1:
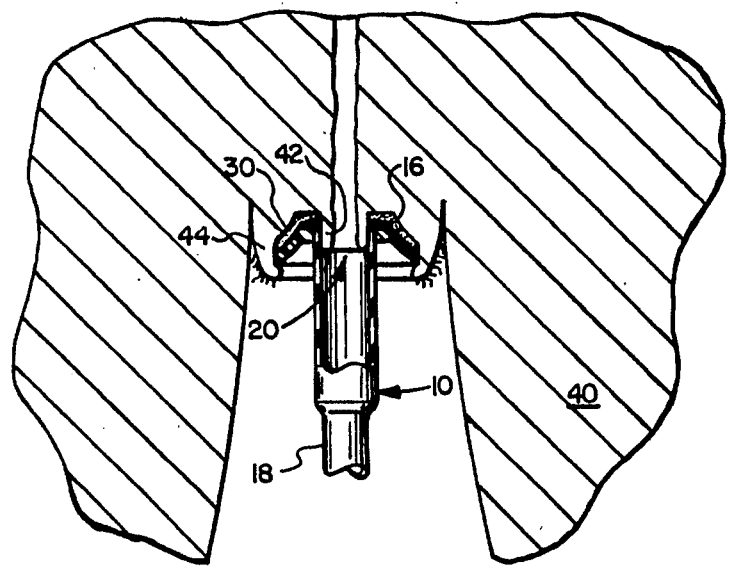
FIG. 1 is a transverse cross-sectional view of an external catheter of the present invention in place on a subject.

The placement of the external catheter is illustrated in FIG. 1 which shows a transverse cross-section of catheter unit 10 and of the external structure of the urogental region of the subject 40.

When catheter unit 10 is in place, labium minora 42 are brought through inlet 20 and into main body 14 of the catheter and channel discharge from the urethra and vagina into the main body of the catheter which empties through outlet tube 18 to a collection system.

Adhesive surface 16 bounds inlet 20 and engages the subject's body between labium minora 42 and labium majora 44 at the cross-section. Adhesive surface 16 extends interiorly in front of the clitoris above the plane of the cross-section and extends posteriorly down to the posterior fourchette below the plane of the cross-section.

The first step in preparing the subject for placement of catheter 10 is to trim the pubic hair in order to prevent entanglement of the hair with the catheter's adhesive surface. Such entanglement would make proper placement difficult and uncomfortable and would substantially impair the ability to attain a leak proof seal. Closely trimming the pubic hair for approximately one half inch surrounding the labium majora has been found sufficient.

The subject's entire urogenital region is then throughly cleansed. Warm water and mile soap are effective for this purpose.

Then a protective dressing is applied to the sensitive tissues which the adhesive surfaces of catheter 10 are to engage. Protective dressing is applied around the clitoris, in between the labium majora and labium minora and down to the posterior fourchette. The subject is now prepared for catheterization. In the preferred embodiment, sterile, disposal catheters are packaged individually and provided with a backing which covers the adhesive surface. Further, in the preferred method of catherization, the device is put in place with the backing still covering the adhesive surface.

The catheter is placed with the periphery of open inlet 20 in position to encircle the clitoris, urethra and vagina, seating between opposing labium majora and labium minora. Further, the labrium minora are brought through inlet 20 into main body 14 of the catheter.

After the placement of the catheter, tabs are pulled to remove the backing and expose adhesive surface 16 on the subject side of catheter 10. Still in position, catheter 10 is pressed firmly against the subject and adhesive surface 16 contacts the subject to securely and sealingly engage around the periphery of inlet 20. The catheter is held in position for a few seconds and then inspected to insure that a tight seal has formed that will not leak.

An alternate embodiment of primary usefulness for young girls packages main body 14 of the catheter separately from adhesive surface 16 which is provided by unassociated double-sided adhesive tape. To affix this embodiment of the present device, the subject is simularly prepared and a first side of the double-sided adhesive tape is affixed to the subject with the removal of the protective backing on that side in the same manner as described above for the unitary embodiment. After the tape is sealingly affixed to the subject and the labium minora are brought through the opening of the tape, the backing is removed from the second side of adhesive tape. The periphery of inlet 20 of main body 14 of the catheter is then sealingly connected to the second side of the adhesive tape. Further, this embodiment de-emphasizes the need for a stabilizer in use for pre-puberty girls.

It is apparent that the device and method of catheterization presented herein permit self-cathterization which is a particularly important attribute for women who suffer from prolonged or intermittent incontinency. The use of this external catheter is safe, produces relatively little discomfort, and does not impair the mobility of the user.

I claim:

1. A pliable flexible external catheter adapted to be affixed to a female human subject having normal external urogenital structures, said catheter comprising:
   a main body of said catheter having an elongated stabilizer and a longitudinal axis;
   an elongated inlet transverse to the longitudinal axis of said main body of said catheter;
   a horizontal and substantially planar first adhesive surface means surrounding and extending from said inlet and on the elongated stabilizer, said first adhesive surface means being adapted to surround and hold the subject's labium minora in said main body through said inlet, and to sealingly engage the catheter to said subject between opposing labium majora and labium minora, extending anteriorly to seal about the clitoris and posteriorly to the fourchette;
   the elongated stabilizer having two opposing transverse sides and two opposing ends, each supporting said first adhesive surface means;
   a second adhesive surface means offset from said first adhesive surface means and cooperating therewith for sealingly engaging the catheter to said subject;
   support means for supporting said second adhesive surface means comprising arcuately downwardly curved and laterally extending shoulders projecting from each of the opposing sides of said elongated stabilizer obliquely away from said inlet at an arcuate curve in relation to said main body; and
   an outlet tube connected to the main body of said catheter opposite said inlet.

2. A pliable flexible external catheter designed to be affixed to a female human subject having normal external urogenital structures, said catheter comprising:
   a main body of said catheter formed of latex rubber and having a longitudinal axis;
   an elongated inlet to said main body of said catheter;
   a first adhesive surface means surrounding said inlet, said first adhesive surface means being adapted to surround and hold the subject's labium minora in said main body through said inlet, and to securely and sealingly engage the catheter to said subject between opposing labium majora and labium minora, extending anteriorly to seal about the clitoris and posteriorly to the fourchette;

a pliable, resilient and substantially planar, elongated stabilizer having two opposing sides and two opposing ends, each supporting said first adhesive surface means;

a second adhesive surface means offset from said first adhesive surface means and cooperating therewith for sealingly engaging the catheter to said subject;

support means for supporting said second adhesive surface comprising pliable and resilient arcuately curved laterally extending shoulders projecting from each of the opposing sides of said elongated stabilizer obliquely away from said inlet at an acute angle in relation to said main body; and an outlet tube formed of latex rubber connected to the main body of said catheter opposite said inlet.

3. An external catheter constructed in accordance with claim 2 wherein said first and second adhesive surfaces are continguous.

* * * * *